United States Patent [19]

Corbett et al.

[11] 3,940,416
[45] Feb. 24, 1976

[54] BENZIMIDAZOLE SULPHONYL CHLORIDES

[75] Inventors: John Roger Corbett, Linton; Albert Percival, Hauxton, both of England

[73] Assignee: Fisons Ltd., England

[22] Filed: Apr. 30, 1974

[21] Appl. No.: 465,675

Related U.S. Application Data

[62] Division of Ser. No. 165,696, July 23, 1971, Pat. No. 3,823,154.

[30] Foreign Application Priority Data

July 29, 1970 United Kingdom............... 36673/70
Mar. 16, 1971 United Kingdom................. 7044/71

[52] U.S. Cl. ............................................ 260/309.2
[51] Int. Cl.$^2$...................................... C07D 235/10
[58] Field of Search................................ 260/309.2

[56] References Cited
UNITED STATES PATENTS

| 2,888,486 | 5/1959 | Gregory | 260/543 R |
| 3,412,101 | 11/1968 | Zwahlen | 260/309.2 |
| 3,658,899 | 4/1972 | Campbell | 260/543 R |
| 3,706,794 | 12/1972 | Horner | 260/543 R |

OTHER PUBLICATIONS

Fieser et al., Reagents for Organic Synthesis, pp. 286, 287, 1158 & 1159, N.Y., Wiley, 1967.
Knobloch et al., Chem. Abst., 1959, Vol. 53, Column 3197.
Roblin et al., Chem. Abst., 1951, Vol. 45, Columns 4670–4671.
Sayapin et al., Chem. Abst., 1970, Vol. 73, No. 45409p.

*Primary Examiner*—Natalie Trousof
*Attorney, Agent, or Firm*—Wenderoth, Lind & Ponack

[57] ABSTRACT

2-Trifluoromethylbenzimidazoles having a sulphamoyl or substituted sulphamoyl substituent on the benzene ring combat mammalian parasites, for example liver fluke in mammals e.g. sheep, and cattle tick and sheep blowfly.

6 Claims, No Drawings

BENZIMIDAZOLE SULPHONYL CHLORIDES

This is a division of application Serial No. 165,696, filed July 23, 1971, now U.S. Patent No. 3,823,154.

This invention relates to parasiticides.

We have discovered that a certain class of substituted benzimidazole is not only of lower mammalian toxicity than neighbouring classes but also has a surprisingly high level of mammalian parasiticidal activity, especially as anthelmintics.

Accordingly, the invention provides a method of combating parasites in or on a mammal, which method comprises administering to the mammal a parasiticidal amount of a compound which is a substituted benzimidazole of formula:

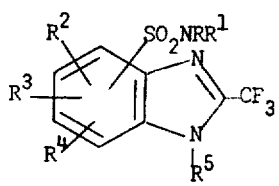

(I)

or a therapeutically acceptable salt thereof, in which

R and $R^1$, which may be the same or different, each represent hydrogen, aryl, substituted aryl (for example aryl substituted by halogen and/or alkyl), alkyl, substituted alkyl (for example alkyl substituted by hydroxy, alkoxy, halogen and/or dialkylamino), cycloalkyl of from 3 to 8 carbon atoms (for example cyclopropyl or cyclohexyl), alkenyl (for example allyl) or alkynyl (for example propargyl), or R and $R^1$, together with the nitrogen atom to which they are attached, form a heterocyclic radical (for example piperidino or morpholino);

$R^2$, $R^3$ and $R^4$ which may be the same or different each represent hydrogen, halogen, nitro, cyano, alkyl, substituted alkyl (for example alkyl substituted by halogen, e.g. trifluoromethyl), alkoxy, aryloxy, alkylthio or an oxygenated derivative thereof (for example —SO alkyl or —$SO_2$ alkyl) arylthio or an oxygenated derivative thereof (for example —SO aryl or —$SO_2$ aryl) or a further $SO_2NRR^1$ group (in which R and $R^1$ are as defined above); and $R^5$ represents hydrogen, alkyl or the group $C(:X)YR^6$ in which X and Y, which may be the same or different, each represent oxygen or sulphur and $R^6$ represents alkyl, aryl, substituted alkyl (for example alkyl substituted by hydroxy, alkoxy and/or halogen), substituted aryl (for example aryl substituted by halogen and/or alkyl), alkenyl (for example allyl), alkynyl (for example propargyl) or cycloalkyl of from 3 to 8 carbon atoms (for example cyclohexyl).

Alkyl in this specification means alkyl of up to 12, usually up to 6, carbon atoms, e.g. methyl, ethyl, normal- or iso-propyl or normal-butyl; alkoxy, alkenyl, alkynyl and alkylthio are analogous. Aryl may be for example phenyl or naphthyl; aryloxy and arylthio are analogous.

The invention provides also a parasiticidal composition comprising such a compound together with a therapeutically acceptable carrier, particularly a sterile carrier.

The invention also provides an anthelmintic composition comprising 150–1500mg of such a compound together with a pharmaceutically acceptable carrier, the composition being in unit dosage form. Thus, it may be in the form of a tablet or a capsule containing the composition. The composition may be solid.

In addition, the invention provides a preferred compound which is a substituted benzimidazole of formula

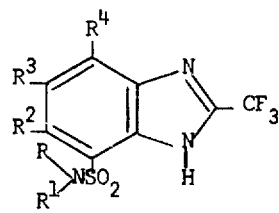

(II)

or a therapeutically acceptable salt thereof, in which

R and $R^1$, which may be the same or different, each represent hydrogen or alkyl of up to 12 carbon atoms, or R and $R^1$, together with the nitrogen atom to which they are attached, form a heterocyclic ring; and $R^2$, $R^3$ and $R^4$, which may be the same or different, each represent a halogen atom. The invention also provides a process for preparing such a compound, which process comprises reacting the corresponding benzimidazole sulphonyl chloride of formula

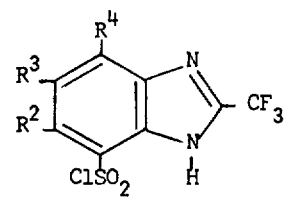

with an amine of formula $HNRR^1$.

The present compounds of formula I may be used to combat external animal parasites, e.g. cattle tick or sheep blowfly. The compounds are however, particularly valuable as anthelmintics.

Usually in the present compounds R and $R^1$, which may be the same or different, each represent hydrogen; phenyl; phenyl substituted by halogen or by alkyl of up to 6 carbon atoms; alkyl of up to 6 carbon atoms; alkyl of up to 6 carbon atoms substituted by hydroxy, alkoxy of up to 6 carbon atoms, halogen or by dialkylamino whose alkyl groups each contain up to 6 carbon atoms; cycloalkyl of 3–8 carbon atoms; allyl; or propargyl or R and $R^1$, together with the nitrogen atom to which they are attached, form a piperidino or morpholino radical;

$R^2$, $R^3$ and $R^4$, which may be the same or different, each represent hydrogen; halogen; nitro; cyano; alkyl of up to 6 carbon atoms; alkyl of up to 6 carbon atoms substituted by halogen; alkoxy of up to 6 carbon atoms; phenyloxy; alkylthio of up to 6 carbon atoms; phenylthio or a further $SO_2NRR^1$ group; and $R^5$ represents hydrogen, alkyl of up to 6 carbon atoms or the group

in which Y represents oxygen or sulphur and $R^6$ represents alkyl of up to 6 carbon atoms; phenyl; alkyl of up to 6 carbon atoms substituted by hydroxy, alkoxy of up to 6 carbon atoms or by halogen; phenyl substituted by halogen or by alkyl of up to 6 carbon atoms; allyl or propargyl.

In a preferred group of the compounds R and $R^1$, which may be the same or different, each represent hydrogen, alkyl of up to 6 carbon atoms, dialkylaminoalkyl whose alkyl groups each contain up to 6 carbon atoms, chlorine-substituted phenyl, hydroxyalkyl of up to 6 carbon atoms, or R and $R^1$, together with the nitrogen atom to which they are attached, form a piperidino radical;

$R^2$, $R^3$ and $R^4$, which may be the same or different, each represent hydrogen or halogen, at least two of them being halogen; and $R^5$ represents hydrogen or $COOR^6$ where $R^6$ represents alkyl of up to 6 carbon atoms.

Any halogen (i.e. chlorine, bromine, iodine or fluorine) is generally chlorine for convenience in preparation. In one embodiment one or none of $R^2$, $R^3$ and $R^4$ represent hydrogen. The $SO_2NRR^1$ group in formula I is often on the 4- or 7- position.

By reason of a combination of low mammalian toxicity and high parasiticidal, especially anthelmintic activity, compared with compounds closely related chemically, it is preferred that the compound be a substituted benzimidazole of formula:

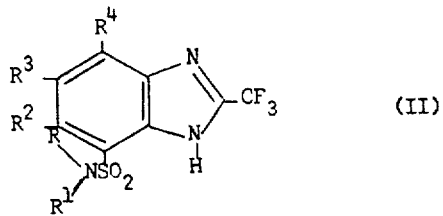

or a therapeutically acceptable salt thereof, in which

R and $R^1$, which may be the same or different, each represent hydrogen or alkyl of up to 12 carbon atoms, or R and $R^1$, together with the nitrogen atom to which they are attached, form a heterocyclic ring; and $R^2$, $R^3$ and $R^4$, which may be the same or different, each represent a halogen atom.

Usually in this preferred group of formula II, R and $R^1$, which may be the same or different, each represent hydrogen or alkyl of up to 12 carbon atoms, or R and $R^1$, together with the nitrogen atom to which they are attached, form a piperidino or morpholino radical.

Preferred within this preferred group are compounds wherein R and $R^1$, which may be the same or different, each represent hydrogen or alkyl of up to 6 carbon atoms, or R and $R^1$, together with the nitrogen atom to which they are attached, form a piperidino radical; and $R^2$, $R^3$ and $R^4$, which may be the same or different, each represent a chlorine or bromine atom.

In the present compounds of formula I, it is preferred that one or preferably both of R and $R^1$ be other than hydrogen.

An especially preferred group of compounds by reason of an exceptionally good combination of low mammalian toxicity and high parasiticidal, especially anthelmintic, activity, is of formula II above where R and $R^1$ each represent an ethyl group and $R^2$, $R^3$ and $R^4$, which may be the same or different, each represent a chlorine or bromine atom.

Particular benzimidazoles are specified in the Examples. Particularly preferred specific compounds are:

5,6,7-trichloro-N,N-diethyl-2-trifluoromethylbenzimidazole-4-sulphonamide;
7-bromo-5,6-dichloro-N,N-diethyl-2-trifluoromethylbenzimidazole-4-sulphonamide;
5,6,7-tribromo-N,N-diethyl-2-trifluoromethylbenzimidazole-4-sulphonamide; and
5,7-dibromo-6-chloro-N,N-diethyl-2-trifluoromethylbenzimidazole-4-sulphonamide;

and their therapeutically acceptable salts.

The present compounds may be prepared by a process which comprises reacting the corresponding benzimidazole sulphonyl chloride of formula

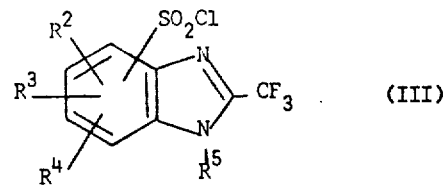

with an amine of formula $HNRR^1$, where R, $R^1$, $R^2$, $R^3$, $R^4$ and $R^5$ are as defined under formula I.

Compounds where $R^5$ is $C(:X)YR^6$, e.g. $COOR^6$ may also be prepared by a process which comprises reacting the corresponding benzimidazole sulphonamide of formula I where $R^2$ represents a hydrogen atom with a chloroformate of formula $ClC(:X)YR^6$, e.g. $ClCOOR^6$.

It will be appreciated that some of the present compounds may exist in tautomeric forms. $R^5$ may be on either of the imidazole nitrogen atoms. For convenience, only one form is named, but the present invention embraces both forms.

Thus, for production of the above-mentioned particularly preferred sulphonamides, the following corresponding sulphonyl chlorides are employed:

5,6,7-trichloro-2-trifluoromethylbenzimidazole-4-sulphonyl chloride;
7-bromo-5,6-dichloro-2-trifluoromethylbenzimidazole-4-sulphonyl chloride;
5,6,7-tribromo-2-trifluoromethylbenzimidazole-4-sulphonyl chloride; and
5,7-dibromo-6-chloro-2-trifluoromethylbenzimidazole-4-sulphonyl chloride.

It will also be appreciated that for reasons of solubility etc., the present substituted benzimidazoles which form such salts may well be used in the form of therapeutically acceptable salts, and whether any particular salt is therapeutically acceptable can of course readily be determined. A salt which is acceptable for external treatment may of course not be acceptable for internal treatment. A salt is therapeutically acceptable for purposes of scope of the present compounds if it is therapeutically acceptable for any of the present treatments.

Suitable salts of the substituted benzimidazoles embraced by the present invention in which $R^5$ represents hydrogen include ammonium salts, metal salts such as for example sodium, potassium, calcium, zinc, copper and magnesium salts, amine salts such as for example methylamine, ethylamine, dimethylamine, triethylamine, ethanolamine, triethanolamine and benzylamine salts. According to a preferred embodiment the salts are alkali metal salts. Generally the alkali metal salts are crystalline solids, readily soluble in water. Especially preferred, however, are N-methyl-glucamine salts.

The salts may be prepared by reacting the benzimidazole in aqueous or aqueous-organic solvent solution or suspension with an alkaline compound of the metal, such as the hydroxide, or with the amine or ammonia, as appropriate. The metal salts may also be prepared by metathesis for example between the alkali metal salt of the benzimidazole and a salt of the metal. Some of the benzimidazoles are also basic and can form salts with strong acids such as hydrochloric acid.

Salts with acids, e.g. strong acids such as hydrochloric acid, may also be formed by reason of the $SO_2NRR^1$ part of the molecule.

The present compounds possess parasiticidal activity. They are particularly valuable as anthelmintics (e.g. as fasciolicides) but they also possess activity against external parasites, e.g. blowfly and tick. For any of these uses the compounds may be used to inhibit infection or to treat an infection already present.

The compounds are generally used in the form of compositions, and these usually contain a therapeutically acceptable carrier and/or surface active agent. The compositions may be prepared by a process comprising admixing the ingredients. For some treatments the composition should of course be sterile.

The carrier may be water. Many of the salts of the substituted benzimidazoles embraced by the invention are water-soluble, and these may be used as aqueous solutions with or without surface active agents or organic solvents.

If desired, the substituted benzimidazole or salt thereof may be dissolved in a water immiscible solvent, such as for example a hydrocarbon of boiling point 130° to 250°C, which may contain a dissolved surface active agent.

The substituted benzimidazole or salt thereof may be admixed with a surface active agent with or without a carrier.

The carrier may be a solid, e.g. talc, chalk, gypsum or earths, with or without surface active agents.

The main use envisaged is as anthelmintics. For anthelmintic use, the compounds may be administered orally or parenterally, and may be administered as a pharmaceutical preparation with a pharmaceutically acceptable carrier, e.g. in a tablet or capsule, or may be admixed with the drinking water or food for the animals. Animals in which use is envisaged include domestic and farm animals, e.g. sheep, pigs, cows, horses, dogs and cats, and animals for use in laboratories, e.g. mice, rats, hamsters and guinea pigs. The compounds may also be administered to human beings. They are particularly active against liver fluke (*Fasciola hepatica*).

Formulations for adding to drinking water may include surface active agents to ensure satisfactory solution or dispersion.

Formulations for adding to foods may consist of the compound alone or be mixed with physiologically acceptable carriers such as talc, chalk, gypsum or earths, with or without surface active agents.

The compounds may be formulated by impregnating or coating a granule, for example a gypsum granule, with them.

A composition may contain as carrier a foodstuff for the animal.

The surface active agents may comprise anionic compounds for example soaps, fatty sulphate esters such as dodecyl sodium sulphate, fatty aromatic sulphonates such as alkyl-benzene sulphonates or butyl napthalene sulphonates, more complex fatty sulphonates such as the amide condensation product of oleic acid and N-methyl taurine or the sodium sulphonate of dioctyl succinate.

The surface active agents may also comprise non-ionic surfact active agents such as for example condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide. The surface active agents may also comprise cationic agents such as for example cetyl trimethylammonium bromide.

The term "surface active agent" is used in the broad sense to cover materials variously called wetting agents, emulsifying agents and dispersing agents. Such agents are well known in the parasiticide art.

The compositions may contain other parasiticidal compounds or other compounds which stimulate the growth or health of the animal.

The present compounds are useful because they possess pharmacological activity in animals. In particular, the compounds are anthelmintics as indicated by anthelminthic tests in rats and sheep. For this use, the dosage rate will, of course, depend on such factors as the particular compound employed, its toxicity, the treatment desired and the animal treated. In general, however, the dosage is about 2–250mg of active ingredient per kilogram of body weight. A single dose may be sufficient, or it may be repeated if necessary. For the larger mammals, a suitable dose is about 150–1500 mg. The compounds are also parasiticides for external animal parasites as indicated by tests on sheep and cows. For such use, the amount of active ingredient may be between 0.01 and 0.5% by weight of the total composition, e.g. spray, dip or drench, use.

The invention is illustrated by the following Examples, in which parts and percentages are by weight and temperatures are in degrees Centigrade unless otherwise indicated.

EXAMPLE 1

5,6,7-Trichloro-N,N-diethyl-2-trifluoromethylbenzimidazole-4-sulphonamide.

5,6,7-Trichloro-2-(trifluoromethyl)-4-benzimidazolesulphonyl chloride (22 parts) in dry acetone (80 parts) was added dropwise to a solution of diethylamine (12 parts) in dry acetone (16 parts). The temperature was kept below 30° and the reaction mixture stirred for 2 hours. The solvent was evaporated and the residue treated with 6N hydrochloric acid. The solid product was collected, washed with water and dried (23 parts). Recrystallisation from toluene (charcoal) gave the required product as pale coloured needles (21.6 parts; m.p.[melting point] 152°–154°; 89.7%).

Found: C, 33.8; H, 2.45; N, 9.6. $C_{12}H_{11}Cl_3F_3N_3O_2S$ requires: C, 33.95; H, 2.6; N, 9.9%.

EXAMPLES 2-20

The following were prepared by a similar method:

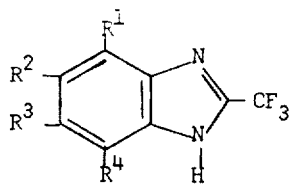

EXAMPLES 21-26

The following compounds of formula II were prepared by a similar method:

| Example No. | R | R¹ | R² | R³ | R⁴ | Melting point |
|---|---|---|---|---|---|---|
| 21 | $C_2H_5$ | $C_2H_5$ | Cl | Cl | Br | 188-190 |
| 22 | $C_2H_5$ | $C_2H_5$ | Br | Br | Br | 175-177 |
| 23 | $C_2H_5$ | $C_2H_5$ | Br | Cl | Br | 177-178 |
| 24 | $C_2H_5$ | $C_2H_5$ | Br | Cl | Cl | 153-155 |
| 25 | $C_2H_5$ | $C_2H_5$ | Cl | Br | Cl | 169-171 |
| 26 | $CH_3$ | $CH_3$ | Cl | Br | Cl | 203-205 |

| Ex. No. | $R_1$ | $R_2$ | $R_3$ | $R_4$ | m.p. | Recrystallising solvent | Found C | Found H | Found N | Requires C | Requires H | Requires N |
|---|---|---|---|---|---|---|---|---|---|---|---|---|
| 2 | $SO_2N(CH_3)_2$ | Cl | Cl | Cl | 243-244° | xylene | 30.55 | 2.0 | 10.45 | 30.3 | 1.8 | 10.6 |
| 3 | $SO_2N(nC_3H_7)_2$ | Cl | Cl | Cl | 145-146° | petrol (80-100°) | 36.85 | 3.5 | 9.35 | 37.15 | 3.35 | 9.3 |
| 4 | $SO_2N(isoC_3H_7)_2$ | Cl | Cl | Cl | 179-180° | petrol (100-120°) | 36.75 | 3.15 | 9.3 | 37.15 | 3.35 | 9.3 |
| 5 | $SO_2N(nC_4H_9)_2$ | Cl | Cl | Cl | 93-95° | petrol (40-60°) | 39.8 | 3.9 | 8.9 | 39.95 | 4.0 | 8.75 |
| 6 | $SO_2NHC_4H_9$-n | Cl | Cl | Cl | 152-153° | petrol (100-120°) | 34.1 | 2.8 | 9.65 | 33.95 | 2.6 | 9.9 |
| 7 | $SO_2NH(CH_2)_2N(C_2H_5)_2 \cdot HCL$ | Cl | Cl | Cl | 241-243° | nitromethane | 33.3 | 3.2 | 11.0 | 33.35 | 3.4 | 11.1 |
| 8 | $SO_2NH$-(2,6-Cl$_2$C$_6$H$_3$) | Cl | Cl | Cl | 284-286° | nitromethane | 32.35 | 1.5 | 7.85 | 32.75 | 1.0 | 8.15 |
| 9 | $SO_2N(CH_2CH_2OH)_2$ | Cl | Cl | Cl | 165-166° | nitromethane | 31.35 | 2.5 | 9.05 | 31.55 | 2.45 | 9.2 |
| 10 | $SO_2N$(piperidino) | Cl | Cl | Cl | 236-238° | ethanol | 35.45 | 2.6 | 9.55 | 35.75 | 2.55 | 9.6 |
| 11 | $SO_2N(CH_3)_2$ | Cl | Cl | H | 169-171° | nitromethane | 32.8 | 2.5 | 11.35 | 33.15 | 2.25 | 11.6 |
| 12 | $SO_2N(C_2H_5)_2$ | Cl | Cl | H | 129-131° | petrol (80-100°) | 36.65 | 2.85 | 10.65 | 36.95 | 3.1 | 10.75 |
| 13 | $SO_2N(nC_3H_7)_2$ | Cl | Cl | H | 103-104° | petrol (80-100°) | 40.35 | 3.45 | 10.2 | 40.2 | 3.85 | 10.05 |
| 14 | $SO_2N(isoC_3H_7)_2$ | Cl | Cl | H | 146-147° | nitromethane | 40.25 | 3.75 | 10.15 | 40.2 | 3.85 | 10.05 |
| 15 | $SO_2N(nC_4H_9)_2$ | Cl | Cl | H | 60-62° | petrol (below 40°) | 42.65 | 4.3 | 9.3 | 43.05 | 4.5 | 9.4 |
| 16 | $SO_2NHnC_4H_9$ | Cl | Cl | H | 145-146° | petrol (100-120°) | 36.70 | 3.05 | 10.45 | 36.95 | 3.1 | 10.75 |
| 17 | $SO_2NHC_2H_5$ | Cl | Cl | H | 89-91° | toluene | 33.2 | 2.25 | 11.35 | 33.15 | 2.25 | 11.6 |
| 18 | Cl | H | $SO_2N(C_2H_5)_2$ | H | 142-143° | benzene | 40.25 | 3.4 | 11.6 | 40.5 | 3.7 | 11.8 |
| 19 | $NO_2$ | H | $SO_2N(C_2H_5)_2$ | H | 120-121° | petrol (100-120°) | 39.05 | 3.3 | 15.3 | 39.35 | 3.6 | 15.3 |
| 20 | H | H | $SO_2N(C_2H_5)_2$ | H | 89-91° | dilute ethanol | 44.85 | 4.4 | 13.05 | 44.5 | 4.6 | 12.75 |

EXAMPLE 27

Isopropyl 5,6-dichloro-4-(diethylsulphamoyl)-2-trifluoromethyl)-1-benzimidazolecarboxylate Isopropyl chloroformate (2 parts) in acetone (8 parts) was added to a solution of 5,6-dichloro-N,N-diethyl-2-(trifluoromethyl)-4-benzimidazolesulphonamide (6 parts) in acetone (16 parts) containing triethylamine (1.6 parts), stirred at room temperature for 1 hour, filtered off the hydrochloride and the filtrate was evaporated to dryness. The residue was recrystallized from ethanol to give white needles of the required product (3.2 parts; m.p. 133°–135°).

Found: C, 40.2; H, 3.7; N, 9.1. $C_{16}H_{18}Cl_2F_3N_3O_4S$ requires: C, 40.35; H, 3.8; N, 8.8%.

EXAMPLE 28

Similarly ethyl 5,6-dichloro-4-(diethylsulphamoyl)-2-trifluoromethyl)-1-benzimidazolecarboxylate was prepared (m.p. 168°–169°; from ethanol).

Found: C, 38.65; H, 3.8; N, 8.8. $C_{15}H_{16}Cl_2F_3N_3O_4S$ requires: C, 38.95; H, 3.5; N, 9.1%.

EXAMPLE 29

1 ml aliquots of an acetone solution of the product of Example 1, containing 1000, 300, 100, 30 and 10 ppm (parts per million), were applied to cotton wool dental rolls 1 cm diameter × 2 cms. After drying these were placed in glass vials 2 cms diameter × 5 cms and closed by a cotton wool plug.

The treated cotton wool rolls were then impregnated with 1 ml sheep serum and infested with first instar larvae of the sheep blowfly, *Lucilia sericata*, then held at 25°C for 24 hours.

The precentage mortality of the parasites was then recorded, when it was found that the treatments had killed more than 95% as compared with less than 5% in controls.

EXAMPLES 30 to 35

The experiment described in Example 29 was applied to the products of Examples 3, 6, 11, 12, 13 and 16. The same result was obtained.

EXAMPLES 36 to 38

The experiment described in Example 29 was also applied to the products of Examples 4, 5 and 14, but with the following dosage rates: 1000, 300, 100 and 30 ppm. The same result was obtained.

EXAMPLE 39

1 ml aliquots of an acetone solution of the product of Example 1, containing 1000, 300 and 100 ppm, were applied to filter papers, 9 cm in diameter. These were allowed to dry then folded into quadrant shaped packets.

The treated papers were then infested with first stage larvae of the cattle tick, *Boophilus microplus*, closed by a metal clip and held at 25°C for 24 hours.

The percentage mortality of the ticks was then recorded, when it was found that each of the treatments had killed more than 95% of the ticks as compared with less than 5% in controls.

EXAMPLES 40 to 47

The experiment described in Example 39 was also applied to the products of Examples 2, 3, 4, 5, 6, 11, 12 and 13. The same result was obtained.

EXAMPLE 48

The experiment described in Example 39 was also applied to the product of Example 14, except that the dosage rates were 1000, 300, 100 and 30 ppm. The result was the same.

EXAMPLES 49 to 57

Three week old rats (Wistar strain) were infected orally with 30 metacercaria of the liver fluke, *Fasciola hepatica*. Forty days after infection, when most of the flukes had become established in the bile duct, the rats were administered orally with 2% suspensions in tragacanth of the benzimidazole derivatives listed below at the rates indicated. Five rats were used at each dosage rate of each compound. The dosage rates used were governed by the acute oral $LD_{50}$ to rats as determined by preliminary toxicological studies.

Six days after administration, the rats were killed and the bile duct dissected to determine the number of mature flukes surviving. Results are tabulated below as the percentage fluke reduction in comparison with unmedicated control animals.

| Ex. No. | Compound | Rate of treatment (mg/kg) | | | |
|---|---|---|---|---|---|
| | | 187 | 93 | 46 | 23 |
| 49 | Product of Example 1 | | | 91 | 45 |
| 50 | Product of Example 21 | | | 85 | |
| 51 | Product of Example 22 | | 90 | 65 | |
| 52 | Product of Example 23 | | 90 | 78 | |
| 53 | Product of Example 2 | | | | 60 |
| 54 | Product of Example 3 | | 80 | | |
| 55 | Product of Example 6 | 90 | 40 | | |
| 56 | Product of Example 24 | | | 85 | 77 |
| 57 | Product of Example 25 | | | 80 | 60 |

EXAMPLE 58

Example 49 was carried out but with a 0.66% tragacanth suspension of the compound. The same result was obtained.

EXAMPLES 59 to 66

Three week old rats (Wistar strain) were infected orally with 30 metacercaria of the liver fluke, *Fasciola hepatica*. Fourteen days after infection, when a high percentage of the migrating flukes were still in the liver parenchyma, the rats were administered orally with 2% suspensions in tragacanth of the benzimidazole derivatives listed below at the rates indicated. Five rats were used at each dosage rate of each compound. The dosage rates used were governed by the acute oral $LD_{50}$ to rats as determined by preliminary toxicological studies.

Six days after administration, the rats were killed and their livers minced to liberate the surviving immature flukes. These were compared with unmedicated control animals and the results tabulated below as the percentage fluke reduction.

| Ex. No. | Compound | Rate of treatment (mg/kg) | | | |
|---|---|---|---|---|---|
| | | 187 | 93 | 46 | 23 |
| 59 | Product of Example 1 | | | 98 | 96 |
| 60 | Product of Example 21 | | | 88 | 50 |
| 61 | Product of Example 22 | | 82 | 70 | |
| 62 | Product of Example 23 | | 98 | 90 | |
| 63 | Product of Example 2 | | | | 60 |
| 64 | Product of Example 6 | 98 | | | |
| 65 | Product of Example 24 | | | 98 | 80 |
| 66 | Product of Example 25 | | | 96 | 78 | by administering the compound to two sheep four weeks after infection and to two other sheep twelve weeks after infection.

All the sheep, as well as untreated control animals, were slaughtered 13 weeks after infection and the flukes present in each animal were counted.

Efficiency of the treatment was assessed by comparing the number of flukes in treated animals with the number in the untreated controls.

The results are shown below:

| Dose Rate (mg/kg) | Age of Infection at Time of Treatment (Weeks) | No. of Flukes recovered | % Reductions |
|---|---|---|---|
| 6 | 4 | 29 9 | 75 |
| 6 | 12 | 27 6 | 82 |
| 12 | 4 | 0 2 | 99 |
| 12 | 12 | 0 0 | 100 |
| Untreated controls | | 38 111 | |

EXAMPLE 67

Three week old rats (Wistar strain) were infected orally with 30 metacercaria of the liver fluke, *Fasciola hepatica*. Forty days after infection, when most of the flukes had become established in the bile duct, the product of Example 3 was administered orally as a 1.35% tragacanth/arachis oil solution/suspension at a rate equivalent to 94 mgs active ingredient per Kg of body weight. The dosage rate used was governed by the acute oral $LD_{50}$ as determined by preliminary toxicological studies. Five rats were used.

Six days after the compound was administered, the rats were killed and the bile duct dissected to determine the number of mature flukes surviving. It was found that the reduction of flukes in each treatment was 80% in comparison with unmedicated controls.

EXAMPLE 68

Three week old rats (Wistar strain) were infected orally with 30 metacercaria of the liver fluke, *Fasciola hepatica*. Forty days after infection, when most of the flukes had become established in the bile duct, the product of example 6 was administered orally as a 3.7% tragacanth/arachis oil solution/suspension at rates equivalent to 188 and 94 mgs active ingredient per Kg of body weight. The dosage rates used were governed by the acute oral $LD_{50}$ as determined by preliminary toxicological studies. Five rats were used at each dosage rate.

Six days after the compound was administered, the rats were killed and the bile duct dissected to determine the number of mature flukes surviving. It was found that the reduction of flukes in the respective treatments was 90 and 40% in comparison with unmedicated controls.

EXAMPLE 69

Sheep known to be free from liver fluke disease were each infected with 300 *Fasciola hepatica* metacercaria.

The product of Example 1 was administered by subcutaneous injection of an aqueous solution of its N-methyl-glucamine salt. The effect of the product against immature and adult liver flukes was determined A dose of 12 mg/Kg was completely effective against fluke infections of 4 weeks and 12 weeks duration.

The lower dose of 6 mg/Kg gave a high degree of activity against both ages of fluke although complete cures were not achieved.

EXAMPLE 70

The experiment described in Example 68 was also applied to the product of Example 7.

It was found that the reduction of flukes in the treatments at 188 and 94 mg/kg was respectively 75 and 65% in comparison with unmedicated controls.

The benzimidazole sulphonyl chlorides of formula III which may be used in the preparation of the present active compounds may be prepared by reacting the corresponding benzimidazole sulphonic acid with thionyl chloride, preferably in the presence of dimethylformamide as catalyst. The use of dimethylformamide has been found to result in a surprising increase in yield. The benzimidazole sulphonic acid may be prepared by sulphonation of the corresponding benzimidazole derivative of formula

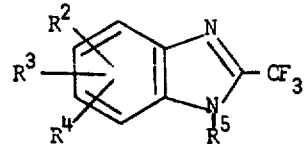

where $R^2$, $R^3$, $R^4$ and $R^5$ are as defined under formula I, suitably by means of oleum. These processes are illustrated by the following Examples.

EXAMPLE 71 a. 4,5,6-trichloro-2-trifluoromethylbenzimidazole (145 parts) was added gradually to stirred oleum (1260 parts) and the mixture then refluxed for 2 hours. After cooling, the mixture was poured into water (3000 parts), the temperature being allowed to rise to near boiling. The mixture was cooled to room temperature overnight and the crystalline product was filtered off, washed with water and dried to give 165.9 parts (92% yield) of 5,6,7-trichloro-2-trifluoromethylbenzimidazole-4-sulphonic acid.

EXAMPLE 72 b. The 5,6,7-trichloro-2-trifluoromethylbenzimidazole-4-sulphonic acid (155 parts) was added to a stirred mixture of thionyl chloride (770 parts) and dimethylformamide (24 parts). A vigorous effervescence took place, and when this had subsided the mixture was slowly heated to reflux temperature (80°C) and maintained at this temperature for three hours. The reaction mixture was then cooled and the solid crystals filtered off, washed with benzene (160 parts) and dried to give 5,6,7-trichloro-2-trifluoromethylbenzimidazole-4-sulphonyl chloride (138 parts), melting point (with decompoition) 208°–209°C. Evaporation of the filtrate yielded a further 10 parts of the product, giving a total yield of 148 parts (91% yield).

EXAMPLE 73 c. Diethylamine (102 parts) was added dropwise to a suspension of the 5,6,7-trichloro-2-trifluoromethylbenzimidazole-4-sulphonyl chloride (136 parts) in acetone (400 parts) cooled in an ice bath to maintain a temperature of about 30°C. After the addition of all the diethylamine, the mixture was stirred for 15 minutes and then poured into excess ice/water. The resulting solution was acidified with concentrated hydrochloric acid to precipitate a cream solid which was filtered off, washed with water and dried to give 5,6,7-trichloro-N,N-diethyl-2-trifluoromethylbenzimidazole-4-sulphonamide (144 parts, 97% yield), melting point 155°–157°C.

EXAMPLES 74–79

The following other compounds were prepared by processes analogous to those of Examples 71–73:

| Compound | melting point | yield stage (a) | yield stage (b) | yield stage (c) |
|---|---|---|---|---|
| 7-bromo-5,6-dichloro-N,N-diethyl-2-trifluoromethyl-benzimidazole-4-sulphonamide | 183–5°C | 94% (Example 74) | 91.6% (Example 75) | 96% (Example 76) |
| 5,7-dibromo-6-chloro-N,N-diethyl-2-trifluoromethyl-benzimidazole-4-sulphonamide | 173–5°C | 94% (Example 77) | 89.6% (Example 78) | 89% (Example 79) |

We claim:

1. A benzimidazole sulphonyl chloride of the formula:

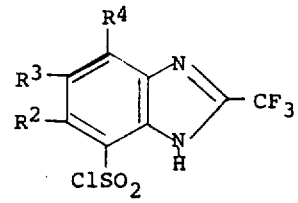

wherein $R^2$, $R^3$ and $R^4$, which may be the same or different, each represent halogen.

2. A benzimidazole sulphonyl chloride according to claim 1 wherein $R^2$, $R^3$ and $R^4$, which may be the same or different, each represent a chlorine or bromine atom.

3. A benzimidazole sulphonyl chloride according to claim 1 which is 5,6,7-trichloro-2-trifluoromethylbenzimidazole-4-sulphonyl chloride.

4. A benzimidazole sulphonyl chloride according to claim 1 which is 7-bromo-5,6-dichloro-2-trifluoromethylbenzimidazole-4-sulphonyl chloride.

5. A benzimidazole sulphonyl chloride according to claim 1 which is 5,6,7-tribromo-2-trifluoromethyl-benzimidazole-4-sulphonyl chloride.

6. A benzimidazole sulphonyl chloride according to claim 1 which is 5,7-dibromo-6-chloro-2-trifluoromethylbenzimidazole-4-sulphonyl chloride.

\* \* \* \* \*